(12) United States Patent
Blain

(10) Patent No.: US 7,527,649 B1
(45) Date of Patent: May 5, 2009

(54) INTERVERTEBRAL IMPLANT AND RELATED METHODS

(75) Inventor: Jason Daniel Blain, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 20 days.

(21) Appl. No.: 10/367,441

(22) Filed: Feb. 14, 2003

Related U.S. Application Data

(60) Provisional application No. 60/357,435, filed on Feb. 15, 2002.

(51) Int. Cl.
*A61F 2/44* (2006.01)
(52) U.S. Cl. .................... 623/17.11; 623/17.16
(58) Field of Classification Search ... 623/17.11–17.16; 606/60, 61, 99
See application file for complete search history.

(56) References Cited

U.S. PATENT DOCUMENTS

| | | |
|---|---|---|
| 2,401,856 A | 6/1946 | Brock |
| 4,501,269 A | 2/1985 | Bagby |
| 4,820,305 A | 4/1989 | Harms |
| 4,961,740 A | 10/1990 | Ray |
| 5,015,247 A | 5/1991 | Michelson |
| 5,026,373 A | 6/1991 | Ray |
| 5,458,638 A | 10/1995 | Kuslich |
| 5,484,437 A | 1/1996 | Michelson |
| 5,522,899 A | 6/1996 | Michelson |
| 5,591,235 A | 1/1997 | Kuslich |
| 5,593,409 A | 1/1997 | Michelson |
| 5,609,635 A | 3/1997 | Michelson |
| 5,609,637 A | 3/1997 | Biedermann |
| 5,702,449 A * | 12/1997 | McKay ................. 623/17.16 |
| 5,702,451 A | 12/1997 | Biedermann |
| 5,702,453 A | 12/1997 | Rabbe |
| 5,741,253 A | 4/1998 | Michelson |
| 5,776,196 A | 7/1998 | Matsuzaki |
| D403,069 S | 12/1998 | Drewry |
| 5,885,299 A | 3/1999 | Winslow |
| 5,888,224 A | 3/1999 | Beckers |
| 5,897,556 A | 4/1999 | Drewry |
| 5,968,098 A | 10/1999 | Winslow |
| 5,972,031 A * | 10/1999 | Biedermann et al. ...... 623/17.16 |
| 5,989,290 A | 11/1999 | Biedermann |
| 6,019,763 A | 2/2000 | Nakamura |
| 6,019,793 A | 2/2000 | Perren et al. |
| 6,039,762 A * | 3/2000 | McKay ................... 623/17.11 |
| D425,989 S | 5/2000 | Michelson |
| 6,086,613 A * | 7/2000 | Camino et al. ........... 623/17.16 |
| 6,093,201 A | 7/2000 | Cooper |
| 6,143,032 A | 11/2000 | Schafer |
| 6,149,651 A * | 11/2000 | Drewry et al. ................. 606/61 |
| 6,159,215 A | 12/2000 | Urbahns |
| 6,179,839 B1 | 1/2001 | Weiss |
| 6,200,348 B1 | 3/2001 | Biedermann |
| 6,206,924 B1 | 3/2001 | Timm |
| RE37,161 E | 5/2001 | Michelson |
| 6,245,108 B1 | 6/2001 | Biscup |
| D450,122 S | 11/2001 | Michelson |
| D454,953 S | 3/2002 | Michelson |
| 6,375,681 B1 | 4/2002 | Truscott |

(Continued)

*Primary Examiner*—Pedro Philogene
(74) *Attorney, Agent, or Firm*—Jonathan Spangler; Rory Schermerhorn

(57) ABSTRACT

An intervertebral implant (mesh cage) for placement between adjacent vertebral bodies and dimensioned to receive osteogenetic or bone growth inducing material for promoting fusion of the adjacent vertebral bodies.

16 Claims, 2 Drawing Sheets

U.S. PATENT DOCUMENTS

| | | |
|---|---|---|
| 6,379,654 B1 | 4/2002 | Gebreselassie |
| D460,188 S | 7/2002 | Michelson |
| 6,447,543 B1 | 9/2002 | Studer |
| 6,524,341 B2 | 2/2003 | Lang |
| 6,562,074 B2 | 5/2003 | Gerbec |
| 6,572,654 B1 | 6/2003 | Santilli |
| 6,585,770 B1 * | 7/2003 | White et al. ............. 623/17.11 |
| 6,652,584 B2 | 11/2003 | Michelson |
| 6,666,866 B2 | 12/2003 | Martz et al. |
| 6,679,883 B2 * | 1/2004 | Hawkes et al. ................ 606/61 |
| 6,689,167 B2 * | 2/2004 | Bagby .................... 623/17.11 |
| 6,695,851 B2 | 2/2004 | Zdeblick et al. |
| 6,776,798 B2 | 8/2004 | Camino |
| 6,849,093 B2 * | 2/2005 | Michelson ............... 623/17.15 |
| 2001/0056302 A1 | 12/2001 | Boyer |
| 2002/0068978 A1 | 6/2002 | Camino |
| 2002/0099443 A1 | 7/2002 | Messerli |
| 2003/0074064 A1 | 4/2003 | Gerbec |

* cited by examiner

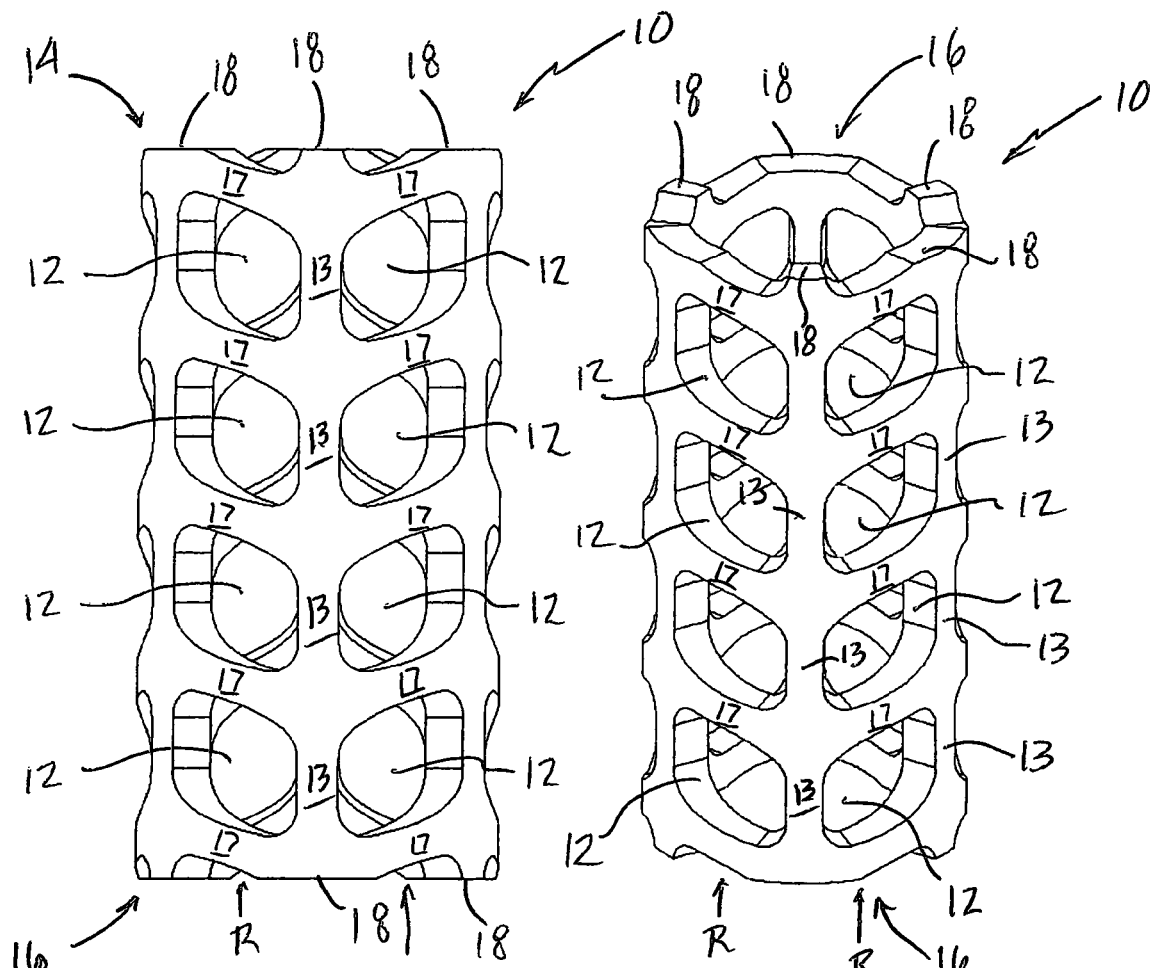
*Figure 1*     *Figure 2*
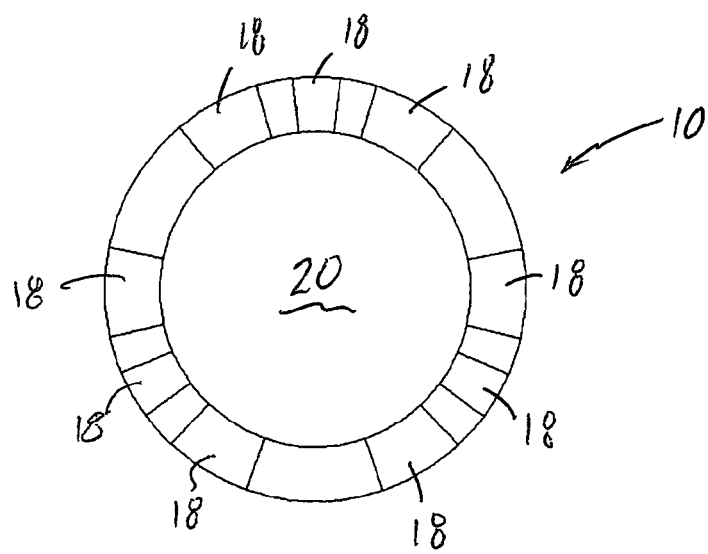
*Figure 3*

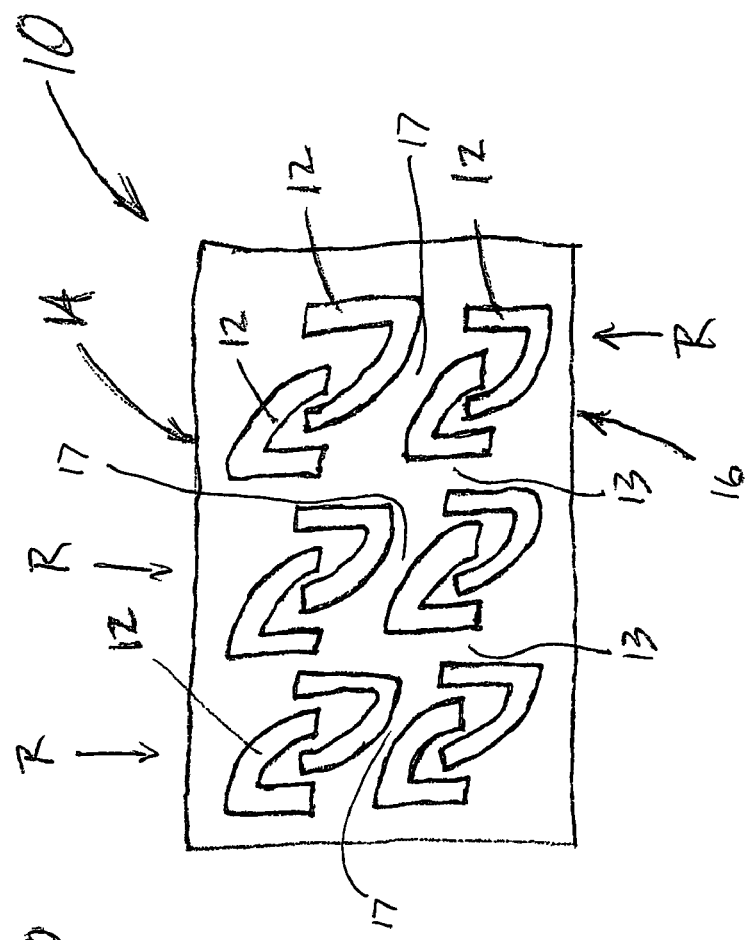
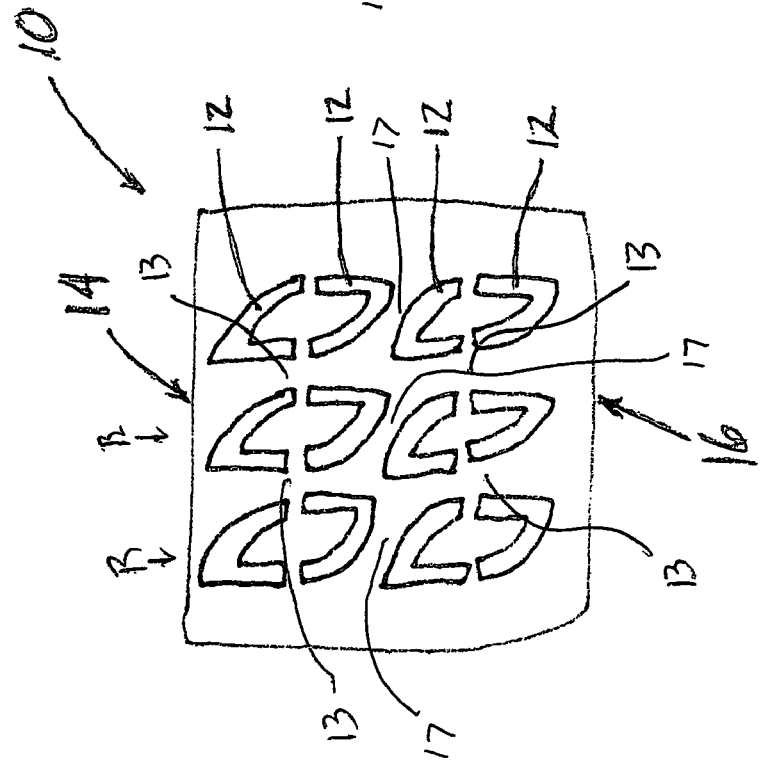

INTERVERTEBRAL IMPLANT AND RELATED METHODS

CROSS-REFERENCE TO RELATED APPLICATION

This application claims the benefit of the filing date under 35 USC 119(e) of provisional application entitled "Intervertebral Implant and Related Methods," Ser. No. 60/357,435 filed Feb. 15, 2002, and fully incorporated herein by reference.

BACKGROUND OF THE INVENTION

1. Field of the Invention

The present invention relates to an intervertebral implant and related methods. More specifically, the present invention relates to a cage structure for placement between adjacent vertebral bodies and dimensioned to receive osteogenetic or bone growth inducing material for promoting fusion of the adjacent vertebral bodies.

2. Discussion of Related Art

The repair and reconstruction of bony structures is sometimes accomplished by directly fixing adjacent bony structures to each other, such as by a plate. In other cases, bone growth inducing material can be introduced between the adjacent bony structures, which over time results in a solid bony connection. In some instances, the adjacent bony structures are not sufficiently strong to maintain their patency as the bone heals or the bone grows between the adjacent structures through the bone growth inducing material. In these instances, mesh structures or cages have been provided to engage the adjacent bony structures to provide additional stability. The cages are generally hollow and can be configured to contact the harder cortical bone of the adjacent bony structures. The hollow portion of the cages can be filled with bone growth inducing material.

SUMMARY OF THE INVENTION

The present invention involves a mesh cage of unique and improved construction. The mesh cage of the present invention is dimensioned to be positioned in between adjacent vertebral bodies and to receive osteogenetic or bone growth-inducing material. The mesh cage has sufficient structural rigidity to avoid collapse during use and to maintain an effective space between the vertebral bodies during use. By positioning the mesh cage in the intervertebral space, and disposing osteogenetic or bone growth-inducing material within the hollow interior of the cage, interbody fusion is effectively promoted. The mesh cage of the present invention may be provided having any number of different shapes (in cross-section), including but not limited to generally circular (forming a cylinder), generally oval, oblong, generally rectangular, and/or having a generally concave and/or convex outer peripheral edge (forming, by way of example, a generally "banana" shaped cage). The mesh cage includes a plurality of non-symmetrical openings (such as, by way of example, apertures forming various alphanumeric characters, such as "N" and "V"). The mesh cage may also be equipped with apertures (separate from, or the same as, those described above) capable of engaging with tools for placing the mesh cage within the intervertebral space. The mesh cage of the present invention may be constructed from any number of suitable biocompatible materials, including but not limited to titanium (commercially pure or alloy), ceramic, stainless steel, bone allograft, and any number of biodegradable materials. The mesh cage may be dimensioned in a variety of fashions depending upon the particular application. For example, by way of example only and not limitation, the mesh cage may be provided having a wall thickness ranging between 0.5 millimeters to 10 millimeters, a cross-sectional width ranging between 5 millimeters to 50 millimeters, a cross-sectional length ranging between 5 millimeters to 50 millimeters, and a height ranging between 3 millimeters to 125 millimeters.

BRIEF DESCRIPTION OF THE DRAWINGS

The principles of the present invention will be apparent with reference to the following drawings, in which like reference numerals denote like components:

FIG. 1 is a side elevational view of an intervertebral implant according to the present invention, having asymmetrical apertures with a peripheral shape in the form of stylized alphanumeric characters "N" and "V" mated in vertical relation;

FIG. 2 is a perspective view of the intervertebral implant shown in FIG. 1;

FIG. 3 is a top elevational view of the intervertebral implant shown in FIG. 1;

FIG. 4 is a side elevational view of an intervertebral implant according to a second embodiment, having asymmetrical shapes in the form of the stylized alphanumeric characters "N" and "V" in separated and vertical relation; and FIG. 5 is a side elevational view of an intervertebral implant according to a third embodiment, having asymmetrical shapes in the form of stylized alphanumeric characters "N" and "V" in separated, staggered and vertical relation.

DESCRIPTION OF THE SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present invention contemplates a mesh cage dimensioned to be positioned in between adjacent vertebral bodies and to receive osteogenetic or bone growth-inducing material. The mesh cage has sufficient structural rigidity to avoid collapse during use and to maintain an effective space between the vertebral bodies during use. By positioning the mesh cage in the intervertebral space, and disposing osteogenetic or bone growth-inducing material within the hollow interior of the cage, interbody fusion is effectively promoted.

FIGS. 1-3 show an intervertebral implant (in the form of a mesh cage) 10 according to one aspect of the present invention. The mesh cage 10 has a generally cylindrical shape and elongated and generally asymmetrical apertures 12. In the embodiment shown, the asymmetrical apertures have a peripheral shape in the form of stylized alphanumeric characters "N" and "V" mated in vertical relation. The apertures 12 are arranged in vertical rows R disposed in alternating or "mirrored" orientation with respect to each adjacent row. According to an aspect of the present invention, the apertures 12 are disposed such that a substantially vertical support 13 exists in between each adjacent row R of apertures 12, and angled buttress members 17 exist above and below the apertures and extend angularly downward from one substantially vertical support 13 to another. The substantially vertical support 13 advantageously presents an area of increased structural support, particularly to vertical loading. By creating the intervertebral implant 10 to include a plurality of substantially vertical supports 13, the implant 10 is advantageously equipped with improved loading characteristics, which may be a significant advantage in orthopedic and, more particularly spinal, application.

The mesh cage 10 includes an upper region or edge 14 and a lower region or edge 16 which, according to a preferred embodiment, include engagement members 18 for engaging with the vertebral endplate in use. The engagement members 18 may preferably form part of the periphery of the apertures 12 as the result of manufacture and/or cutting by a surgeon during use. An internal chamber 20 extends between the upper and lower edges 14, 16. The chamber 20 is dimensioned to receive osteogenetic and/or bone growth-inducing materials therein, including but not limited to bone morphogenic protein (BMP).

The mesh cage 10 may be introduced into the intervertebral space in any number of suitable approaches (anterior, posterior, postero-lateral and/or lateral) and may be introduced via any number of commercially available or suitably fashioned inserter devices. The inserter may be dimensioned to removably engage the mesh cage 10, such as by introducing a post (threaded or non-threaded) or other element into one or more of the apertures 12 (or other apertures provided solely for engagement with such an inserter). With the mesh cage 10 rigidly coupled to the inserter, the mesh cage 10 may be introduced into the invertebral space and thereafter released once in the proper position.

According to further aspects of the present invention, the asymmetrical apertures 12 may be provided as two separate stylized alphanumeric characters, as opposed to the joined or mated relation between the stylized alphanumeric characters ("N" and "V" as shown in FIGS. 1-3). For example, as shown in FIG. 4, the intervertebral implant 10 may be equipped having asymmetrical shapes in the form of the stylized alphanumeric characters "N" and "V" in separated and vertical relation. As shown in FIG. 5, the intervertebral implant 10 may have asymmetrical apertures 12 in the form of stylized alphanumeric characters "N" and "V" in separated, staggered, and vertical relation. In both instances, the apertures 12 are disposed in rows R such that vertical supports 13 exist in between each adjacent row, and angled buttress members 17 exist above and below pairs of the stylized alphanumeric characters "N" and "V" and extend angularly downward from one substantially vertical support 13 to another. Again, this provides added structural integrity to the intervertebral implant 10, particularly for vertical loading.

The mesh cage of the present invention may be constructed from any number of suitable biocompatible materials, including but not limited to titanium (commercially pure or alloy), ceramic, stainless steel, bone allograft, and any number of biodegradable materials. The mesh cage may be dimensioned in a variety of fashions depending upon the particular application. For example, by way of example only and not limitation, the mesh cage may be provided having a wall thickness ranging between 0.5 millimeters to 10 millimeters, a cross-sectional width ranging between 5 millimeters to 50 millimeters, a cross-sectional length ranging between 5 millimeters to 50 millimeters, and a height ranging between 3 millimeters to 125 millimeters. The mesh cage of the present invention may also be provided having any number of different shapes (in cross-section), including but not limited to generally circular (forming a cylinder) as shown, generally oval, oblong, generally rectangular, and/or having a generally concave and/or convex outer peripheral edge (forming, by way of example, a generally "banana" shaped cage).

What is claimed is:

1. An intervertebral implant, comprising:
 a structure having a first end for contacting a first vertebral body, a second end for contacting a second vertebral body, an interior chamber extending between said first and second ends, a plurality of substantially vertical supports extending from said first end to said second end, a plurality of angled buttress members extending angularly downward from one of said substantially vertical supports to another of said substantially vertical supports, and at least one aperture formed through said structure, said aperture having a generally asymmetrical shape relative to an axis extending generally perpendicularly between said first and second ends of said structure and through a center point of said aperture.

2. The intervertebral implant of claim 1 and further, wherein said generally asymmetrical shape comprises an alphanumeric character.

3. The intervertebral implant of claim 1 and further, wherein said generally asymmetrical shape comprises a stylized alphanumeric character.

4. The intervertebral implant of claim 1 and further, wherein said generally asymmetrical shape comprises a stylized "N" alphanumeric character and a stylized "V" alphanumeric character, said stylized "N" and "V" alphanumeric characters being asymmetric relative to said axis.

5. The intervertebral implant of claim 1 and further, wherein said structure includes a plurality of generally asymmetrical apertures provided in rows and said at least one substantially vertical support is positioned in between each row.

6. The intervertebral implant of claim 1 and further, wherein said generally asymmetrical shape comprises a stylized "N" alphanumeric character and a stylized "V" alphanumeric character, said stylized "N" and "V" alphanumeric characters being asymmetric relative to said axis and mated in vertical relation.

7. The intervertebral implant of claim 1 and further, wherein said generally asymmetrical shape comprises a stylized "N" alphanumeric character and a stylized "V" alphanumeric character, said stylized "N" and "V" alphanumeric characters being asymmetric relative to said axis and in separated and vertical relation.

8. The intervertebral implant of claim 1 and further, wherein said generally asymmetrical shape comprises a stylized "N" alphanumeric character and a stylized "V" alphanumeric character, said stylized "N" and "V" alphanumeric characters being asymmetric relative to said axis and in separated, staggered, and vertical relation.

9. A method of providing an intervertebral implant, comprising:
 providing a structure having a first end for contacting a first vertebral body, a second end for contacting a second vertebral body, a plurality of vertical supports extending from said first end to said second end, a plurality of angled buttress members extending angularly downward from one of said substantially vertical supports to another of said substantially vertical supports, and an internal chamber extending between said first and second ends; and
 forming at least one aperture through said structure, said aperture having a generally asymmetrical shape relative to an axis extending generally perpendicularly between said first and second ends of said structure and through a center point of said aperture.

10. The method of claim 9 and further, wherein said generally asymmetrical shape comprises an alphanumeric character.

11. The method of claim 9 and further, wherein said generally asymmetrical shape comprises a stylized alphanumeric character.

12. The method of claim 9 and further, wherein said generally asymmetrical shape comprises a stylized "N" alphanumeric character and a stylized "V" alphanumeric character, said stylized "N" and "V" alphanumeric characters being asymmetric relative to said axis.

13. The method of claim 9 and further, wherein said structure includes a plurality of generally asymmetrical apertures provided in rows and said at least one substantially vertical support is positioned in between each row.

14. The method of claim 9 and further, wherein said generally asymmetrical shape comprises a stylized "N" alphanumeric character and a stylized "V" alphanumeric character, said stylized "N" and "V" alphanumeric characters being asymmetric relative to said axis and mated in vertical relation.

15. The method of claim 9 and further, wherein said generally asymmetrical shape comprises a stylized "N" alphanumeric character and a stylized "V" alphanumeric character, said stylized "N" and "V" alphanumeric characters being asymmetric relative to said axis and in separated and vertical relation.

16. The method of claim 9 and further, wherein said generally asymmetrical shape comprises a stylized "N" alphanumeric character and a stylized "V" alphanumeric character, said stylized "N" and "V" alphanumeric characters being asymmetric relative to said axis and in separated, staggered, and vertical relation.

* * * * *